United States Patent
Park et al.

(10) Patent No.: US 10,724,037 B2
(45) Date of Patent: *Jul. 28, 2020

(54) METHOD FOR IMPROVING MEMORY USING CCNY INHIBITOR

(71) Applicant: KOREA INSTITUTE OF SCIENCE AND TECHNOLOGY, Seoul (KR)

(72) Inventors: Mikyoung Park, Seoul (KR); Eunsil Cho, Seoul (KR); Jung-Hwa Hong, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/052,139

(22) Filed: Aug. 1, 2018

(65) Prior Publication Data
US 2018/0346911 A1    Dec. 6, 2018

Related U.S. Application Data

(63) Continuation-in-part of application No. 15/214,422, filed on Jul. 19, 2016, now Pat. No. 10,131,909.

(30) Foreign Application Priority Data

Jul. 20, 2015 (KR) .................. 10-2015-0102254

(51) Int. Cl.
| | | |
|---|---|---|
| *C12N 15/113* | (2010.01) | |
| *A61K 31/7088* | (2006.01) | |
| *C07K 16/40* | (2006.01) | |
| *G01N 33/50* | (2006.01) | |
| *A61K 39/395* | (2006.01) | |
| *A61P 25/28* | (2006.01) | |

(52) U.S. Cl.
CPC ........ *C12N 15/113* (2013.01); *A61K 31/7088* (2013.01); *A61K 39/395* (2013.01); *A61P 25/28* (2018.01); *C07K 16/40* (2013.01); *G01N 33/5023* (2013.01); *G01N 2500/10* (2013.01)

(58) Field of Classification Search
CPC .............. C12N 15/113; C12N 2310/14; C12N 2310/531; C12N 2740/15043; C12Q 2600/158; C12Q 1/6883; C12Q 2600/136; C07K 16/18; C07K 2317/76
See application file for complete search history.

(56) References Cited

FOREIGN PATENT DOCUMENTS

WO     2009/033743 A1    3/2009

OTHER PUBLICATIONS

Cho et al. Cyclin Y inhibits plasticity-induced AMPA receptor exocytosis and LTP. Sci Rep. Jul. 29, 2015;5:12624. doi: 10.1038/srep12624.*
Chan-Yen Ou et al, Two Cyclin-Dependent Kinase Pathways Are Essential for Polarized Trafficking of Presynaptic aomponents, Cell, 141, May 28, 2010, pp. 846-858, Elsevier Inc.
Ammar H Hawasli et al. Cyclin-dependent kinase 5 governs learning and synaptic plasticity via control of NMDAR degradation, Nature Neuroscience, May 27, 2007, pp. 880-886, vol. 10, No. 7.
Park et al., CYY-1/Cyclin Y and CDK-5 Differentially Regulate Synapse Elimination and Formationfor Rewiring Neural Circuits, Neuron 70, May 26, 2011, pp. 742-757.
Yue et al, Cell Cycle Protein Cyclin Y Is Associated With Human Non—Small-Cell Lung Cancer Proliferation and Tumorigenesis, Clinical Lung Cancer, Jan. 2011, pp. 43-50, vol. 12, No. 1.
Li-En Jao et al. Efficient multiplex biallelic zebrafish genome editing using a CRISPR nuclease system, Aug. 20, 2013, pp. 13904-13909, vol. 110.
Richard Morris, Developments of a water-maze procedure for studying spatial learning in the rat, Journal of NeuroScience Methods, Apr. 3, 1984, pp. 47-60, vol. 11.
D. Reisel et al., Spatial memory dissociations in mice lacking GluR1, Nature neuroscience, Aug. 19, 2002, pp. 868-873, vol. 5, No. 9.
David J. Sanderson et al, The Role of Habituation in Hippocampus-Dependent Spatial Working Memory Tasks: Evidence From GluAl AMPA Receptor Subunit Knockout Mice, Hippocampus 22, Dec. 1, 2010, pp. 981-994.

* cited by examiner

*Primary Examiner* — Gregory S Emch
(74) *Attorney, Agent, or Firm* — Goldilocks ZONE IP LAW

(57) ABSTRACT

The present invention relates to a composition for improving memory including a Cyclin Y (CCNY) inhibitor as an active ingredient. More specifically, the present invention relates to a method for improving memory in a subject comprising administering the composition for improving memory to the subject.
The present invention may reveal a CCNY-oriented molecular mechanism with respect to learning and memory, help understand causes of brain diseases associated with memory problems, and ultimately be applied in the treatment and diagnosis of brain memory disorders such as dementia.

1 Claim, 8 Drawing Sheets
(6 of 8 Drawing Sheet(s) Filed in Color)
Specification includes a Sequence Listing.

[FIG. 1]
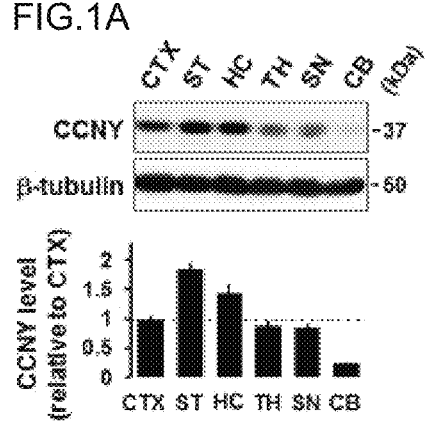
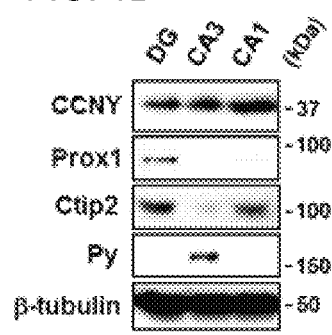
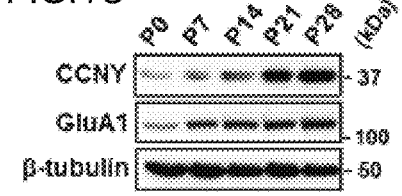
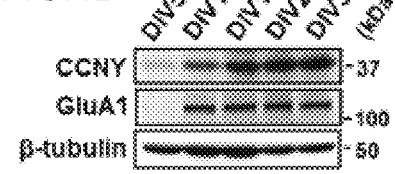
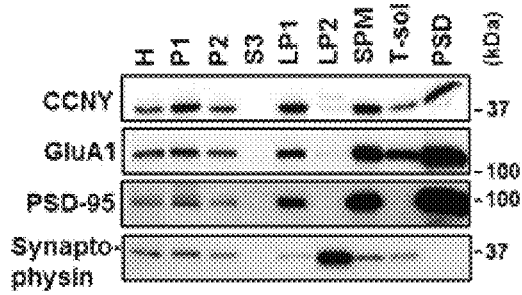

[FIG. 2]
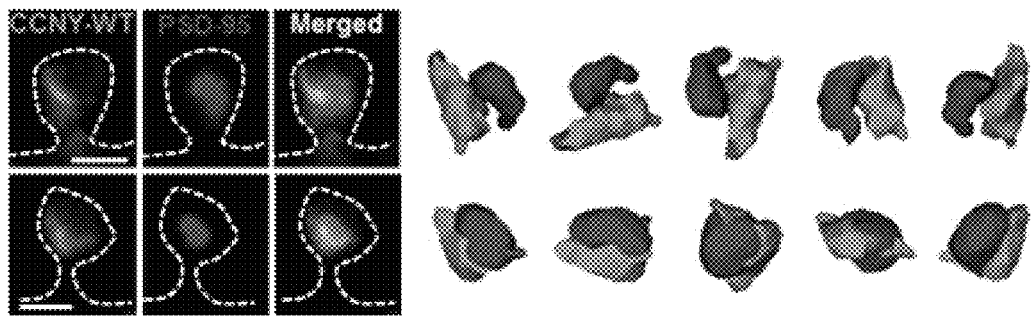
[FIG. 3]
FIG. 3 A
1: 5'-GAGTCTCTTCATTAACCAT-3'
2: 5'-GTACACCATCAAATGTGTA-3'
3: 5'-GTGTAGCTCTTGCGATATA-3'
4: 5'-GTGCCACCAGATTATGACA-3'
FIG. 3B
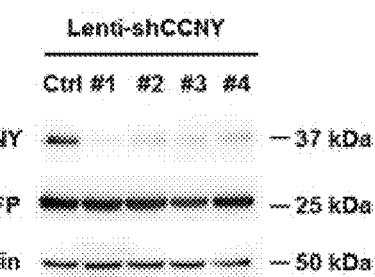
FIG. 3C
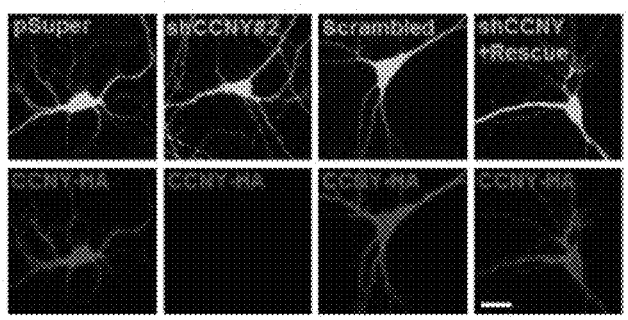
FIG. 3D
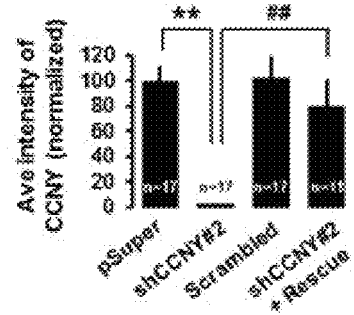

[FIG. 10]
FIG. 10A
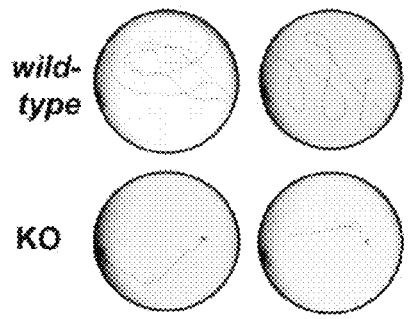
FIG. 10B
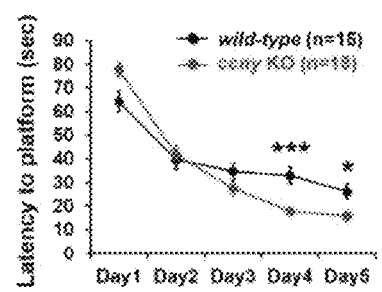
FIG. 10C
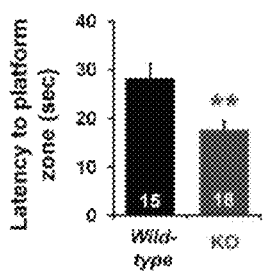
FIG. 10D
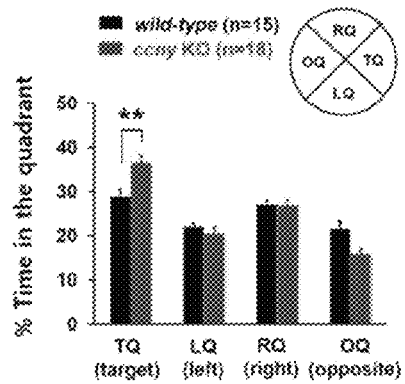
FIG. 10E
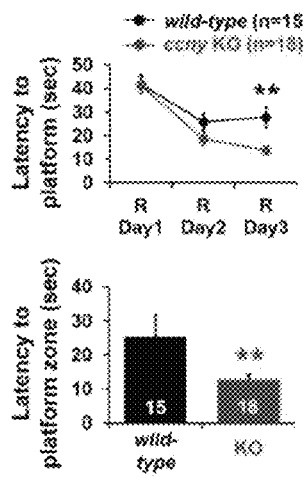
FIG. 10F
FIG. 10G
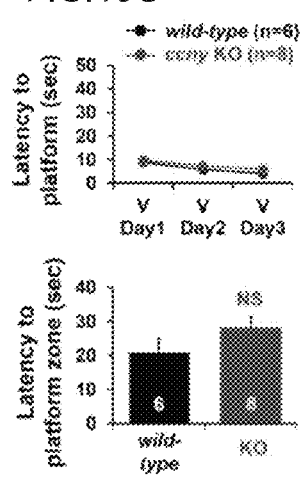
FIG. 10H

[FIG. 11]
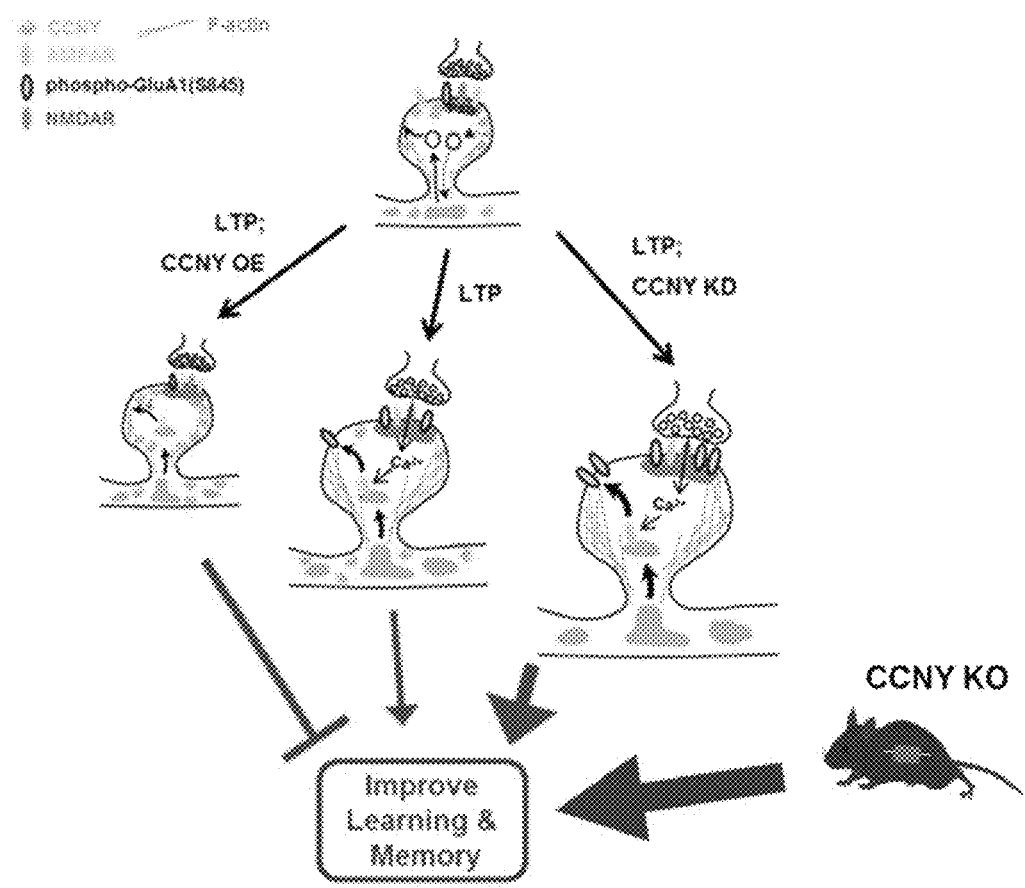

SEQUENCE LISTING

```
<160> NUMBER OF SEQ ID NOS: 6

<210> SEQ ID NO 1
<211> LENGTH: 19
<212> TYPE: RNA
<213> ORGANISM: Artificial Sequence
<220> FEATURE:
<223> OTHER INFORMATION: CCNY shRNA

<400> SEQUENCE: 1
augguuaaug aagagacuc                                                    19

<210> SEQ ID NO 2
<211> LENGTH: 19
<212> TYPE: RNA
<213> ORGANISM: Artificial Sequence
<220> FEATURE:
<223> OTHER INFORMATION: CCNY shRNA

<400> SEQUENCE: 2
uacacauuug augguguac                                                    19

<210> SEQ ID NO 3
<211> LENGTH: 19
<212> TYPE: RNA
<213> ORGANISM: Artificial Sequence
<220> FEATURE:
<223> OTHER INFORMATION: CCNY shRNA

<400> SEQUENCE: 3
uauaucgcaa gagcuacac                                                    19

<210> SEQ ID NO 4
<211> LENGTH: 19
<212> TYPE: RNA
<213> ORGANISM: Artificial Sequence
<220> FEATURE:
<223> OTHER INFORMATION: CCNY shRNA

<400> SEQUENCE: 4
```

```
ugucauaauc ugguggcac                                              19

<210> SEQ ID NO 5
<211> LENGTH: 19
<212> TYPE: RNA
<213> ORGANISM: Artificial Sequence
<220> FEATURE:
<223> OTHER INFORMATION: scrambled CCNY shRNA control

<400> SEQUENCE: 5
uaauuaugcu auaggucgc                                              19

<210> SEQ ID NO 6
<211> LENGTH: 19
<212> TYPE: DNA
<213> ORGANISM: Artificial Sequence
<220> FEATURE:
<223> OTHER INFORMATION: silent mutations of CCNY(sequence number
      2-resistant)

<400> SEQUENCE: 6
gtacacaatt aaatgtgta                                              19
```

METHOD FOR IMPROVING MEMORY USING CCNY INHIBITOR

CROSS-REFERENCE TO RELATED APPLICATION

This application is a continuation-in-part (CIP) application, pursuant to the provisions of 35 U.S.C. § 120, of prior U.S. patent application Ser. No. 15/214,422 titled "METHOD FOR IMPROVING MEMORY USING CCNY INHIBITOR" by MIKYOUNG PARK et al., filed on Jul. 19, 2016, the entirety of which is incorporated herein by reference for all purposes.

This application claims priority to Korean Patent Application No. 10-2015-0102254, filed on Jul. 20, 2015, and all the benefits accruing therefrom under 35 U.S.C. § 119, the contents of which in its entirety are herein incorporated by reference.

BACKGROUND OF THE INVENTION

1. Field of the Invention

The present invention relates to a composition for improving memory including a Cyclin Y (CCNY) inhibitor as an active ingredient. More specifically, the present invention relates to a method for improving memory in a subject comprising administering the composition for improving memory to the subject.

2. Description of the Related Art

Cyclin Y (CCNY), which is a type of cyclin proteins known as an essential protein regulating cell division, is a relatively novel protein whose functions have not been reported in the cell division related field of cancer biology until 2010 (Yue et al., 2011).

Recently, the fact that CCNY protein simultaneously regulates the elimination and formation of synapses in a single neuron and is thus involved in synapse remodeling has been reported with significance to academic circles (Park et al., 2011). However, neither the function nor the regulation of CCNY in the mammalian nervous system has been unknown. The present invention was completed by proving for the first time that CCNY is involved in synapse remodeling in mammals and revealing that the exocytosis of L-α-amino-3-hydroxy-5-methyl-4-isoxazole propionic acid (AMPA) receptors is facilitated when the CCNY function is decreased by the expression of the short hairpin RNA (shRNA) of CCNY. Since AMPA receptor is well-known for its crucial role in mediating the expression of long-term potentiation (LTP), which underlies learning and memory, the present invention was completed by suggesting that CCNY has a role as a memory molecule in the nervous system.

SUMMARY OF THE INVENTION

It is an object of the present invention to provide a novel use of CCNY as a target of an agent for improving memory by discovering that the CCNY protein, which has newly received attention, inhibits expression of a major memory-mediating receptor on the cell surface.

It is another object of the present invention to provide a method for improving memory in a subject comprising administering the composition for improving memory containing a CCNY inhibitor as an active ingredient to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the characterization on various features of CCNY, which is a novel protein, in the mammalian nervous system by biochemical methods: CCNY expression levels in the various regions of brain (FIG. 1A), in sub-regions of the hippocampus (FIG. 1B), and in various developmental stages (FIGS. 1C and 1D) were observed. CCNY protein was also observed to be expressed in the postsynaptic parts of neurons through subcellular fractionation (FIG. 1E).

FIG. 2 shows that the CCNY protein is localized in the postsynapses of the mammalian excitatory synapses through a high-resolution confocal imaging technique.

FIG. 3 shows that shRNA, which is intended for the knockdown of CCNY function, inhibits CCNY expression. The fact that CCNY expression was knocked down by all four types of CCNY shRNAs (FIG. 3A; #1, #2, #3, and #4 refer to SEQ ID NOS: 1, 2, 3, and 4, respectively) was confirmed by an immunoblot analysis (FIG. 3B). In addition, the specificity of shRNA of SEQ ID NO: 2 to CCNY was confirmed by a rescue experiment (FIGS. 3C and 3D).

FIG. 10 shows that spatial learning and memory is enhanced in ccny KO mice. FIGS. 10A-10D indicate that Morris water maze learning is enhanced in ccny KO mice. Representative trajectories of wild type and ccny KO mice movement during the Morris water maze task (training session Day 5) (FIG. 10A). Latency to platform during the training sessions, Day 1 to 5 (FIG. 10B). Latency to platform zone (FIG. 10C) and time spent in the quadrant (FIG. 10D) during the probe test on Day 6 (FIGS. 10C and 10D). TQ, target quadrant; LQ, left side of the TQ; RQ, right side of the TQ; OQ, opposite side of the TQ. Latency to platform during the reversal learning training sessions, R-Day 1 to 3 (FIG. 10E) and latency to platform zone (FIG. 10F) during the reversal learning probe test on R-Day 4 (FIGS. 10E and 10F). Latency to platform during the visible sessions, V-Day 1 to 3 (FIG. 10G) and latency to platform zone (FIG. 10H) during the visible probe test on V-Day 4 (FIGS. 10G and 10H).

FIG. 11 shows a model of CCNY role in LTP and learning and memory. When the expression level of CCNY protein is decreased, the surface delivery of GluA1 to synapses is facilitated, which may improve learning and memory. In contrast, when the expression level of CCNY protein is increased, the surface delivery of GluA1 to synapses is inhibited, which may in turn cause memory problems. Mouse lacking CCNY proteins shows an improved learning and memory.

DETAILED DESCRIPTION OF THE PREFERRED EMBODIMENTS

Figure 4A:
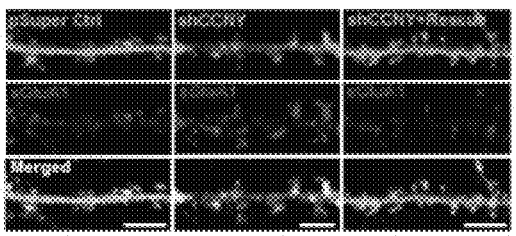
FIG. 4 shows that the surface expression of GluA1, which is one of the main receptors mediating memory, increases when CCNY expression is decreased by shRNA in hippocampal neurons (FIGS. 4A and 4B). There was no difference in the expression level of GluN1, which is a subunit of N-methyl-D-aspartic acid (NMDA) receptors (FIG. 4C). The fact that there was no difference in the total level of GluA1 expression was confirmed by immunocytochemistry (FIGS. 4D and 4E) and immunoblot analysis after producing and infecting CCNY shRNA-expressing lentivirus into the hippocampal neurons (FIG. 4F).

In order to achieve the above object, in an aspect, the present invention provides a composition for improving memory including a CCNY inhibitor as an active ingredient.

Further, the present invention provides a method for improving memory in a subject comprising administering the composition for improving memory to the subject.

Further, the present invention provides a method for preventing or treating cognitive function disorder selected from the group consisting of dementia, Alzheimer's disease, and memory impairment in a subject, comprising administering the composition for improving memory to the subject.

In the present invention, CCNY is a protein that plays an important role in regulating cell cycle and transcription, and it was confirmed that memory may be improved when the gene expression of CCNY gene or activity of CCNY protein is inhibited.

The CCNY inhibitor of the present invention commonly refers to all of the agents that decrease the expression or activity of CCNY. Specifically, the CCNY inhibitor may include all the agents that decrease the expression level or activity of CCNY by decreasing CCNY expression at the transcription level or interrupt the activity thereof after directly or indirectly acting on CCNY.

More specifically, the CCNY inhibitor may be used in forms, such as compounds, nucleic acids, peptides, viruses, etc., that can target and inhibit the expression or activity of CCNY, without limitations. Although not limited thereto, the CCNY inhibitor may also be siRNA, shRNA, or antisense nucleotide, which inhibits the expression of CCNY gene, or an antibody or an aptamer, which inhibits the activity of CCNY protein.

In the present invention, RNA interference (RNAi) is a post-transcriptional gene silencing mechanism where the decomposition of corresponding mRNA occurs by introducing double-stranded RNA (dsRNA) corresponding to the CCNY gene into a cell or an organism. Because multiple cell divisions are sustained before the gene expression is recovered from the RNAi effect, RNAi is a very powerful method for creating a knockout or 'knockdown' that is targeted at the RNA level (Elbashir et al., 2011). For the RNAi technique in gene silencing, a standard molecular biology method is used. dsRNA corresponding to the sequence of a target gene that is to be inactivated may be produced by standard methods such as a simultaneous transcription of both template strands of DNA using a T7 RNA polymerase. For a dsRNA preparation kit used for RNAi, a commercially available product may be used. The method for transfecting dsRNA or a plasmid that is treated to produce dsRNA is a well-known technique.

As used herein, the terms "siRNA" and "shRNA", which are nucleic acid molecules that can mediate RNAi or gene silencing, are used for gene knockdown or gene therapy since they are capable of inhibiting the expression of target genes. shRNA forms a hairpin structure by conjugating to complementary sequences in single stranded oligonucleotides, and becomes siRNA, which is a double stranded oligonucleotide composed of RNA fragment ranging from 21 to 25 nucleotides, when cleaved by dicers in vivo, and conjugates specifically to the mRNA containing complementary sequences in order to inhibit the expression. Therefore, one of ordinary skills in the art may determine whether to use shRNA or siRNA, and if mRNA sequences targeted by shRNA or siRNA are identical, a similar reducing effect on the expression level may be expected. For the purpose of the experiment, siRNA and shRNA may specifically act on CCNY, cleave CCNY mRNA molecules, and induce RNAi, thus inhibiting the CCNY. siRNA or shRNA may be synthesized chemically or enzymatically. The method for producing siRNA or shRNA is not particularly limited and the known methods in the field may be used. Specifically, in one embodiment of the present invention, shRNA that consists of nucleotide sequences of SEQ ID NOS: 1 to 4 is prepared as shRNA for CCNY to inhibit CCNY. As such, shRNA, which is a CCNY inhibitor, may consist of the nucleotide sequence selected from the group consisting of SEQ ID NOS: 1 to 4, and more specifically, the nucleotide sequence of SEQ ID NO: 2.

As used herein, the term "antisense oligonucleotide", which refers to DNA, RNA, or the derivatives thereof containing nucleic acid sequences complementary to specific mRNA sequences, conjugates to complementary sequences within mRNA, and inhibits the translation from mRNA into protein.

A nucleic acid molecule that is an antisense to a nucleic acid coding CCNY may be used as the inhibitor. The 'antisense' nucleic acid includes a nucleic acid sequence that is complementary to a 'sense' nucleic acid coding CCNY (i.e. complementary to a coding strand of a double-stranded cDNA molecule or mRNA sequence). Therefore, the antisense nucleic acid may form a hydrogen bond with the sense nucleic acid. The antisense nucleic acid may be complementary to the entire CCNY coding strand or merely a part (e.g. a coding region) thereof. The antisense nucleic acid molecule may be complementary to the entire coding region of the CCNY mRNA, but an oligonucleotide that is antisense to only a part (e.g. translation initiation region) of a coding or non-coding region of the CCNY mRNA is more preferable. The antisense oligonucleotide may have a length of about 5 to 50 nucleotides. The antisense nucleic acid may be constructed by a chemical synthesis and an enzymatic coupling reaction using well-known methods.

As used herein, the term "antibody" refers to a substance that reacts to an antigen, which is an external material circulating blood or lymph in the in vivo immune system. The antibody, which is globulin protein produced in lymphoid tissues, is also called as an immunoglobulin. For the purpose of the experiment, the antibody may conjugate to CCNY or the ligand protein of CCNY to inhibit CCNY activity.

As used herein, the term "aptamer", which is a single-stranded oligonucleotide, has a size ranging from 20 to 60 nucleotides, and refers to a nucleic acid molecule having a conjugating activity towards target molecules. An aptamer may have various three-dimensional structures according to sequences and high affinity for specific substances as in the antigen-antibody reaction. The aptamer may conjugate to target molecules and inhibit the activity thereof. The aptamer of the present invention may be RNA, DNA, modified nucleic acid, or the mixture thereof, and it may be in straight chain form or cyclic form. Preferably, the aptamer may play a role in conjugating to CCNY and inhibiting CCNY activity. Such aptamers may be prepared by one of ordinary skill in the art from CCNY sequences based on the known methods.

As used herein, the term "subject" refers to all of the animals including humans in need of memory improvement in the present invention. Memory can be improved in a subject by administering the composition for improving memory of the present invention to the subject.

Further, cognitive function disorder selected from the group consisting of dementia, Alzheimer's disease, and memory impairment can be prevented or treated in a subject by administering the composition for improving memory of the present invention to the subject.

As used herein, the term "administration" refers to introducing the composition of the present invention into the subject. Administration may be completed in various routes such as oral or parenteral routes as long as the composition may reach the desired sites.

The composition of the present invention may be administered orally or parenterally when clinically administered. When parenterally administered, the composition of the present invention may be administered in the form of intraperitoneal injection, intrarectal injection, subcutaneous injection, intravenous injection, intramuscular injection, intrauterine epidural injection, cerebrovascular injection, or intrathoracic injection. The composition of the present invention may also be used in the form of general pharmaceutical formulations.

The composition may be used alone or in combination with surgery, radiation therapy, hormone therapy, chemical therapy, and other methods that involve biological response modifiers.

A daily dose of the composition is about 0.0001 mg/kg to 100 mg/kg, and preferably, 0.001 mg/kg to 10 mg/kg. It is preferable to administer the daily dose of the composition once a day or several times a day. However, the range varies depending on the weight, age, sex, health condition, diet, administration time, administration route, excretion rate, degree of disease, etc. of the patient.

The composition may be administered in various parenteral formulations at the time of actual clinical administration. When formulated, the composition is prepared using a diluent, such as a filler, an extender, a binder, a humectant, a disintegrant, a surfactant, etc., and an excipient, which are generally used. Formulations for parenteral administration may include sterilized aqueous solutions, non-aqueous solvents, suspensions, emulsions, lyophilized formulations, and suppositories. As the non-aqueous solvent or suspending agent, propylene glycol, polyethylene glycol, vegetable oil such as olive oil, injectable ester such as ethyl oleate, etc. may be used. As a base for suppositories, Witepsol, Macrogol, Tween 61, cacao butter, laurin butter, glycerogelatin, etc. may be used.

In another aspect of the present invention, the present invention provides a method for screening therapeutic agents for improving memory including:
(1) treating a CCNY-expressing cell line with a candidate test composition or compound;
(2) measuring the mRNA or protein expression level of CCNY in the cell line; and
(3) selecting the candidate test composition or compound having a decreased mRNA or protein expression level of CCNY compared to an untreated control.

The mRNA expression level of CCNY may be measured by any one method selected from the group consisting of real-time polymerase chain reaction (RT-PCR), quantitative or semi-quantitative RT-PCR, northern blot, and DNA or RNA chip methods. The protein expression level of CCNY may be measured by any one method selected from the group consisting of immunohistochemistry, enzyme-linked immunosorbent assay (ELISA), and western blot.

Furthermore, the present invention provides a kit for diagnosis, therapeutic outcomes, or prognosis for memory level, wherein the kit includes any one selected from the group consisting of a nucleic acid complementary to a CCNY gene, a primer or a probe specific to a CCNY gene, and an antibody that conjugates to CCNY protein.

Furthermore, the present invention provides a composition or kit for diagnosis, therapeutic outcomes, or prognosis for preventing or treating cognitive function disorder selected from the group consisting of dementia, Alzheimer's disease, and memory impairment, wherein the composition or kit includes any one selected from the group consisting of a nucleic acid complementary to a CCNY gene, a primer or a probe specific to a CCNY gene, and an antibody that conjugates to CCNY protein.

Hereinafter, the present invention will be described in detail with reference to the following Examples. However, these Examples are for illustrative purposes only, and the scope of the present invention is not limited to these Examples.

1. Preparation of DNA Constructs

CCNY-EGFP was produced by cloning rat CCNY cDNA, which was amplified by PCR from a rat brain cDNA library, into pEGFP-N1 (Clontech Laboratories, Inc.). CCNYmCherry was produced by subcloning rat CCNY cDNA in CCNY-EGFP into pmCherry-N1. PSD95-mCherry, mCherry-N1, mCherry-C1, superecliptic pHluorin (SEP)-GluA1, and pFUGW plasmids were provided by Michael Ehlers (Pfizer Neuroscience, Cambridge, Mass.).

2. Preparation of RNA Interference Constructs and Lentiviral Constructs

Plasmids expressing CCNY shRNA (SEQ ID NO: 1, 2, 3, or 4), which is capable of targeting and knocking down rat CCNY, and a scrambled CCNY shRNA control (SEQ ID NO: 5), which is a control of SEQ ID NO: 2, were produced based on a pSuper vector. The DNA oligonucleotides containing a BglII site, the shRNA sense sequence, a 9-nucleotide hairpin loop region (TTCAAGAGA), and an shRNA antisense sequence at the 5' end, and a HindIII site at the 3' end were synthesized (Integrated DNA Technologies, Inc.), annealed, and ligated into the 5'-BglII/HindIII-3' sites of pSuper (OligoEngine Inc.) and pSuper-EGFP to produce pSuper-(EGFP)-CCNY shRNAs and pSuper-(EGFP)-CCNY scrambled shRNA. For shRNA rescue experiments, an shRNA (SEQ ID NO: 2)-resistant plasmid of CCNY containing two silent mutations, indicated as underlined letters in SEQ ID NO: 6 (5'-GTACAC<u>A</u>AT<u>T</u>AAATGTGTA-3'), in the shRNA (SEQ ID NO: 2) target region was produced using a site-directed mutagenesis (QuikChange Lightning by Agilent Technologies). pSuper-mCherry, pSuper-mCherry-CCNY shRNAs, and pSuper-mCherry-CCNY scrambled shRNA containing mCherry were produced by replacing GFP in pSuper-GFP, pSuper-GFP-CCNY shRNAs, and pSuper-GFP-CCNY scrambled shRNA with mCherry, respectively. When the prepared pSuper-GFP (mCherry)-CCNY shRNA plasmid is expressed in a cell, CCNY shRNA is expressed in the cell to knock down the CCNY expression.

For constructing lentiviral vectors expressing CCNY shRNA, an insert containing a H1 promoter and CCNY shRNA was isolated from pSuper-CCNY shRNAs and subcloned between the HIV-flap and ubiquitin promoters of a FUGW lentiviral vector. For constructing lentiviral vectors expressing CCNY-wild type (CCNY-WT), an insert containing the CCNY-WT was subcloned into an EcoRI/BstBI site of a FUGW lentiviral vector. A FUGW lentiviral vector contains and expresses an EGFP gene through which infection can be determined following the viral production.

3. Production of Lentivirus

The FUGW lentiviral vector including a sequence expressing CCNY-WT or CCNY shRNA, a packaging vector 8.9, and a VSVG envelope glycoprotein vector were co-transfected into HEK 293T cells using Fugene HD (Promega Corporation). Supernatants containing the lentivirus were cultured for 36 hours to 48 hours after transfection and ultracentrifuged at 25,000 rpm to concentrate the lentivirus. The pellets were resuspended in phosphate-buffered saline (PBS), aliquoted, and stored at −80° C.

4. Preparation of Brain Homogenates and Neuronal Cell Lysates

Hippocampi were rapidly excised from an adult rat brain and homogenized with a Dounce glass tissue grinder homogenizer (Wheaton Industries) in an ice-cold homogenization buffer (mM: 320 sucrose, 10 HEPES, 2 EDTA, protease inhibitor cocktail, pH 7.4). The neurons were collected in lysis buffer (mM: 50 TrisHCl, 150 NaCl, 5 EDTA, 1% Triton X-100, a protease inhibitor cocktail, pH 7.4) on ice, lysed by incubation for 1 hour at 4° C., and centrifuged at 1,000 g for 5 minutes at 4° C. Supernatants were collected and protein concentrations were measured by Bradford assays (Bio-Rad Protein Assay kit, Bio-Rad Laboratories, Inc.).

5. Subcellular Fractionation

Subcellular fractionation was performed from postnatal day 30 (P30) Sprague-Dawley (SD) rat forebrain. In brief, the cerebellum and the brainstem were removed from P30 SD rat brain. Forebrains were isolated from three rats and homogenized in buffer A (0.32 M sucrose, 20 mM HEPES, 5 mM EDTA, protease inhibitor cocktail, 1 mM PMSF, pH 7.4) using a glass-teflon homogenizer with 30 strokes. The homogenate was centrifuged for 10 minutes at 1,000 g to produce a nuclear fraction (P1). The supernatant (S1) was centrifuged at 9,200 g for 10 minutes. The resulting pellet was washed by resuspending in buffer A and then centrifuged at 10,000 g for 20 minutes to produce crude synaptosomal fraction (P2). The supernatant was further centrifuged at 12,000 g for 30 minutes to collect a supernatant (S2). S2 was centrifuged at 165,000 g for 2 hours at 4° C. using a NVT90 rotor to produce the cytosolic supernatant (S3) and the microsomal pellet (P3). P2 was resuspended in buffer A and lysed by hypo-osmotic shock using 9 volumes of $H_2O$ and 3 strokes with a glass-Teflon homogenizer, rapidly placed in 4 mM HEPES/5 mM EDTA (pH 7.4), and kept on ice for 30 minutes. The lysate was centrifuged at 25,000 g for 20 minutes at 4° C. to produce a synaptosomal membrane pellet (LP1), a synaptic vesicle, and a cytosolic supernatant (LS1). LS1 was further centrifuged at 165,000 g for 2 hours at 4° C. to produce a synaptic cytosolic supernatant (LS2) and a synaptic vesicle-enriched pellet (LP2) using the NVT90 rotor. LP1 was resuspended and loaded on top of a discontinuous sucrose gradient solution containing 0.8 M, 1 M, and 1.2 M sucrose. The gradient was centrifuged at 150,000 g for 2 hours at 4° C. using a SW41Ti rotor. The cloudy band between 1.0 M and 1.2 M sucrose was collected and diluted in buffer A. The diluted suspension was further centrifuged at 150,000 g for 30 minutes using the SW41Ti rotor to produce a synaptic plasma membrane fraction (SPM). The SPM was resuspended with 0.5% Triton X-100 in buffer A, kept on ice for 15 minutes, and centrifuged at 32,000 g for 20 minutes to divide into soluble and insoluble fractions (Triton X-100 soluble fraction (T-sol) and Postsynaptic density fraction (PSD)). The Triton X-100 insoluble PSD fraction was resuspended in buffer A. 5 μg of protein in each fraction was analyzed by immunoblot.

6. Immunoblot Analysis and Antibodies

Samples containing equal amounts of protein were denatured in SDS buffer, subjected to SDS-PAGE, transferred onto a PVDF membrane, and applied to immunoblot analysis. Protein bands on the immunoblots were visualized by a chemiluminescence method (Millipore) and an imaging documentation system (ImageQuant LAS 4000, GE Healthcare). The images were analyzed using ImageJ. Primary antibodies against CCNY (Proteintech Group), GFP (Roche), GluA1 (Michael Ehlers, Pfizer Neuroscience), phospho-GluA1 (S845) (Thermo Scientific), PSD-95 (Thermo Scientific, 7E3-1B8), synaptophysin (Synaptic Systems), Prox1 (Proteintech Group), Ctip2 (Genetex), Py (D. T. S. Pak, Georgetown University) or β-tubulin (Abcam) were used.

7. Immunocytochemistry

For staining surfaces of AMPA receptors, hippocampal neurons were fixed with 4% paraformaldehyde/4% sucrose in PBS. Then, surface GluA1 was labeled with rabbit anti-GluA1-N (1816, Michael Ehlers, Pfizer Neuroscience or Abcam) for 1 hour at room temperature. Neurons were washed and incubated with Cy3-conjugated anti-rabbit secondary antibodies for 50 minutes at room temperature to visualize the surface GluA1. To stain HA-tagged CCNY or total level of GluA1, hippocampal neurons were fixed with 4% paraformaldehyde/4% sucrose in PBS and were treated with 0.1% Triton X-100 dissolved in PBS. Then, HA-tagged CCNY or total GluA1 was labeled with mouse anti-HA (Convance) or rabbit anti-GluA1-N (Abcam), respectively, for 1 hour at room temperature. Neurons were washed, and incubated with Cy3-conjugated secondary antibodies for 50 minutes at room temperature to visualize HA-tagged CCNY or total level of GluA1.

8. Cell Culture and DNA Transfection

HEK 293T cells were cultured in DMEM (HyClone) supplemented with 10% fetal bovine serum. Hippocampal neuron cultures were prepared from E18 SD rat embryos and maintained for 10 days to 21 days in vitro (DIV) (Park et al., 2006). Neurons were transfected with corresponding plasmids between 10 DIV and 14 DIV using Lipofectamine 2000 (Invitrogen) for 1 day to 2 days or 4 days to 7 days for overexpression or shRNA knockdown experiments, respectively.

9. Live-Cell Imaging

Live neurons grown on a coverslip transfected with a plasmid appropriate for the purpose of the experiment were transferred to an imaging chamber equipped with a heating plate base (Live Cell Instrument, Seoul, Korea), filled with an imaging solution (mM: 120 NaCl, 3 KCl, 2 $CaCl_2$, 2 $MgCl_2$, 15 glucose, 15 HEPES, pH 7.35), and imaged at 32° C. Confocal images were obtained using the Revolution XD System (Andor Technology) equipped with a Yokogawa CSU-X1 spinning disk confocal unit, a 488 nm solid state laser, a 561 nm solid state laser, a 640 nm diode laser, and an Andor 6-line laser combiner. Images were taken with a 60× (NA 1.4) or 100× Plan Apochromat objective (NA 1.4) and a 14-bit iXON3 DU-885 EMCCD camera (Andor Technology) using a Metamorph software program (Molecular Device Inc.). A complete confocal z-sectioning of the region of interest was obtained followed by maximum intensity projection to produce a two-dimensional image using the Metamorph.

For glycine stimulation, neurons were treated with 200 µM glycine in $Mg^{2+}$-free imaging solution containing 0.5 µM TTX, 1 µM strychnine, and 20 µM bicuculline methiodide for 3 minutes to 5 minutes. Then, the neurons were again subjected to live imaging in the imaging solution containing 0.5 µM TTX, 1 µM strychnine, and 20 µM bicuculline methiodide. Neurons at DIV 15 to DIV 17 were used for imaging experiments.

10. Image Analysis and Quantification

To analyze the intensity of surfaces of the AMPA receptors, the integrated intensity of individual puncta of endogenous surface GluA1 on the dendritic protrusions was measured. For the NMDA receptor analysis, the integrated intensity of an NMDA receptor subunit GluN1 from the dendritic protrusions was measured. To evaluate the changes of SEP-GluA1 intensity in the spine, the change in fluorescence intensity was measured as $\Delta F/F_0$. $\Delta F$ was calculated by $F_t-F_0$ where $F_t$ indicates the intensity at each time point and $F_0$ indicates the average intensity of all time points prior to glycine treatment. For 3D volume rendering, a 4D viewer for Metamorph NX software was used. Image XY calibration ranged from 0.02 µm to 0.12 µm per pixel and a distance between planes ranged from 0.15 µm to 0.22 µm.

11. Animals

All experiments handling animals and their embryos were performed in accordance with the guidelines and regulations of the Korea Institute of Science and Technology (KIST). All experimental protocols were approved by the KIST Institutional Animal Care and Use Committee (IACUC; approval number 2018-048).

12. Generation of ccny Knockout (KO) Mice Using CRISPR/Cas9 System

Target Design for ccny Gene.

Single guide RNAs (sgRNAs) were designed using the ZiFiT (http://zifit.partners.org/ZiFiT/) program targeting a N-terminal region of ccny gene. The two complimentary oligos of each sgRNA were annealed and cloned in pT7-gRNA vector, which is a vector designed for synthesis of sgRNA (Jao et al., 2013; Yin et al., 2015).

In Vitro sgRNA Synthesis and Purification.

In vitro transcription of sgRNAs for ccny and short RNA purification were performed using the MEGAshortscript T7 kit (Ambion) according to the manufacturer's instructions.

Microinjection of Zygotes.

Microinjection was performed in the fertilized eggs from C57BL/6J mice. The embryos were harvested in M2 medium and cultured in KSOM medium for 2-3 hours. The mixture of sgRNA (40 ng/µl) and Cas9 protein (80 ng/µl) (Toolgen) was injected into the cytoplasm of the one-cell stage embryos. Injected embryos were cultured in the culture media for 2-3 hours prior to embryo transfer into pseudopregnant female mice (ICR strain).

Genotyping by T7E1 Assay and Sequencing Analysis.

Genomic DNA from toes or tails of the progenies were extracted and subjected to PCR using the primer sets of the gene. PCR amplicons were denatured and slowly reannealed to facilitate heteroduplex formation. The reannealing procedure consisted of a 5 min denaturing step at 95° C., followed by cooling to 85° C. at −2° C. per second and further to 25° C. at −0.1° C. per second. Reannealed amplicons were treated with 5 units of T7 endonuclease I (New England BioLabs) for 30 min at 37° C. and then analyzed by agarose gel electrophoresis. To check for potential off-target effects, the genomic regions encompassing the potential off-target sites with 1- or 2-base mismatch were PCR amplified and subjected to T7E1 assay or sequencing analysis. For PCR genotyping assay on KO line, primer sets for ccny gene were designed as follows:

```
Forward 5'-ACACGGACCTCAGCCGTGAGGA-3',

Reverse 5'-TCCACCATTCCCTGCCAGTCCA-3',

Internal Reverse 5'-CGCTCACCGTCGATGTTTTCCC-3'
```

Figure 9A:
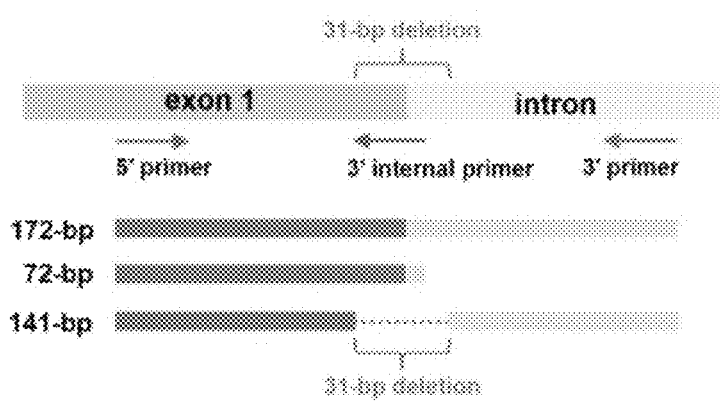
FIG. 9 shows the characterization of a ccny knockout (KO) mouse. The schematic diagram indicates a 31-bp deletion region spanning the first exon and the first intron of ccny gene (FIG. 9A). Locations of primers used for PCR genotyping analysis, the predicted PCR genotyping fragment sizes (FIG. 9A), and the PCR genotyping of wild type (WT), heterozygote (Hetz), and ccny KO (Mut) mice are also shown (FIG. 9B). CCNY protein expression was completely absent in the brain of ccny KO mice (FIG. 9C). CTX, cortex; ST, striatum; HC, hippocampus; TH, thalamus; SN, substantia nigra; CB, cerebellum.
Figure 9B:
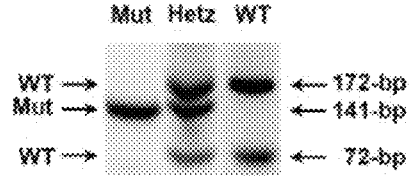

These primers amplify PCR fragments of 172- and 76-bp for wild type, 172-, 141-, and 76-bp for heterozygote, and 141-bp for mutant (FIGS. 9A and 9B).

13. Learning and Memory Behavior Test: Morris Water Maze (MWM)

A round pool with a 120 cm diameter was filled with tap water, and a platform (10 cm diameter, 1.5 cm lower height from the water surface) was placed in a quadrant of the pool. White non-toxic paint was added to make water opaque so that the platform could be hidden from the mice. A water temperature of 21-23° C. was maintained and monitored throughout the experiment. Several visual cues with different shapes were located around the pool so that the mice can see them. For training sessions, mice (8-11 weeks) were allowed to swim and search to find the hidden platform for 90 seconds. If they found the platform within 90 seconds, they were allowed to stay on the platform for 15 seconds and then rescued. If they failed to find the hidden platform within 90 seconds, they were guided gently to the platform by hand and allowed to stay on it for 15 seconds. Each mouse was trained 4 times a day for 5 consecutive days. Latency to the platform was measured and analyzed. For the probe test on the 6$^{th}$ day, the platform was removed, and the trained mice were allowed to search for the platform for 90 seconds. Then, latency to the platform zone and the time spent in each quadrant were measured and analyzed.

For the reversal learning task, 24 to 48 hours after the probe test, the location of the platform was reversed from the original target quadrant to the opposite quadrant. The mice were subjected to the reversal training sessions for 3 days and the reversal probe test on the 4$^{th}$ day. Latency to platform for training sessions and latency to the platform zone for the probe test were measured and analyzed (J Neurosci Methods. 1984 May; 11(1):47-60).

For a visible test, all visible cues around the platform were removed, and a flag was placed on the platform. The mice were trained for 3 days, and then the visible probe test was performed on the 4$^{th}$ day. Latency to platform for training sessions and latency to the platform zone for the probe test were measured and analyzed. Measurements and analyses for the animal behavior experiments were performed using EthoVision XT 13 software (Noldus).

11. Result #1

To study the characteristics of CCNY in the nervous system, an adult rat brain was divided by regions and the expression patterns were observed by western blot analysis. As indicated in FIG. 1A, CCNY exhibits a relatively high expression level in the hippocampus (HC), striatum (ST), cortex (CTX), etc. The hippocampus is a main part of the brain used as a model system by many researchers in the field of synaptic plasticity and CCNY expression was observed in sub-regions of the hippocampus (DG; dentate gyrus, CA3; cornu ammonis 3, CA1; cornu ammonis 1) (FIG. 1B). The expression of CCNY protein in the hippocampus was increased in vivo (FIG. 1C) and in vitro (FIG. 1D) during development. CCNY is also largely distributed in the postsynaptic density (PSD) of neurons (FIG. 1E and FIG. 2). The fact that CCNY expression is high in the hippocampus and CCNY is largely distributed in the PSD fraction suggests that CCNY would play an important role for the synaptic plasticity of the hippocampus.

12. Result #2

Next, it was investigated whether CCNY regulates the expression of AMPA receptors on the neuronal surface. AMPA receptors mediate most excitatory synaptic transmissions in the mammalian central nervous system to glutamate-gated ion channels. As a result, the regulation of the number of AMPA receptors in postsynaptic sites plays an important role in synaptic transmission. In order to observe whether CCNY regulates the neuronal surface expression of AMPA receptors in a characteristic manner, loss-of-function and gain-of-function experiments were performed on CCNY. As a part of the loss-of-function experiment, the function of CCNY was knocked down using an shRNA system. A total of four types (SEQ ID NO: 1, 2, 3, or 4) of lentiviruses, each expressing its own shRNA, were produced and used for infecting primary cultured hippocampal neurons. As a result, a significant decrease in CCNY expression was confirmed by immunoblot analysis (FIG. 3B). In addition, through a rescue experiment, it was confirmed that shRNA of SEQ ID NO: 2 had specificity only to CCNY and inhibited the CCNY expression (FIGS. 3C and 3D), and that the shRNA of SEQ ID NO: 2 may be used for the CCNY knockdown experiment.

Figure 4B:
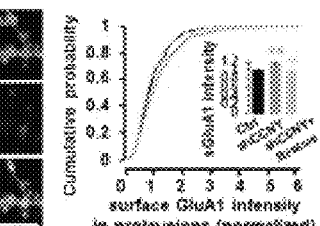
Figure 4C:
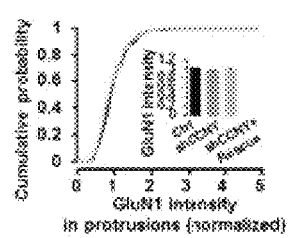
Figure 4D:
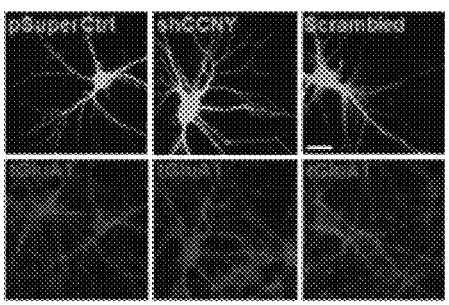
Figure 4E:
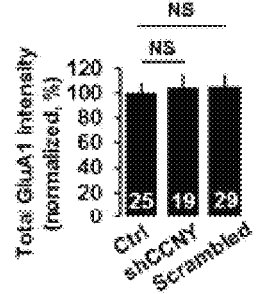
Figure 4F:
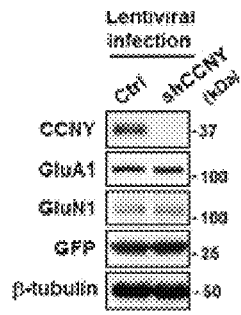
Figure 5A:
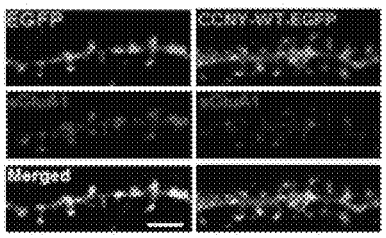
FIG. 5 shows that surface GluA1 expression is reduced when CCNY protein is overexpressed in the hippocampal neurons (FIGS. 5A and 5B). There was no significant difference in the expression level of GluN1 (FIG. 5C). The fact that there was no difference in the total level of GluA1 expression was confirmed by immunocytochemistry (FIGS. 5D and 5E) and immunoblot analysis after producing and infecting CCNY shRNA-overexpressing lentivirus into the hippocampal neurons (FIG. 5F).
Figure 5B:
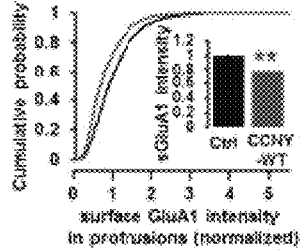
Figure 5C:
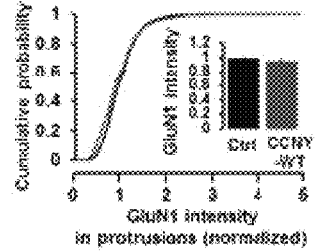
Figure 5D:
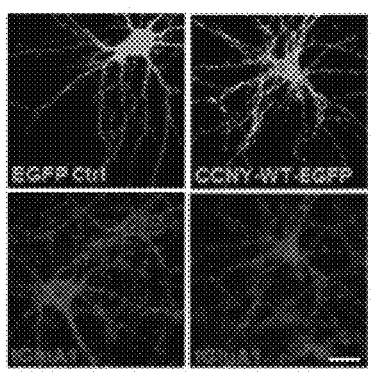
Figure 5E:
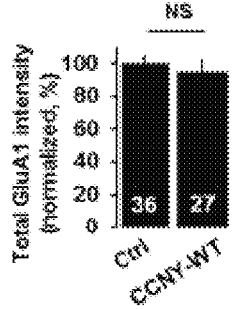
Figure 5F:
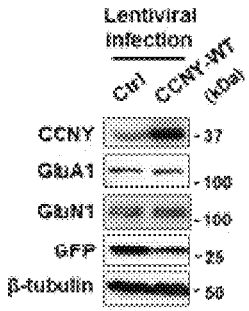

When the CCNY expression in hippocampal neurons was decreased by shRNA, an increase in the surface expression of GluA1, which is one of the main receptors mediating memory, was observed with no change of GluN1 expression level (FIGS. 4A, 4B, and 4C). The fact that there was no change in the total level of GluA1 expression was confirmed by immunocytochemistry (FIGS. 4D and 4E) and immunoblot analysis after producing and infecting CCNY shRNA-expressing lentivirus into the cultured hippocampal neurons (FIG. 4F). In addition, when the CCNY protein was overexpressed in hippocampal neurons, a decrease in the surface expression of GluA1 was observed with no change of GluN1 expression level (FIGS. 5A, 5B, and 5C). Through immunocytochemistry (FIGS. 5D and 5E) and immunoblot analysis (FIG. 5F), it was confirmed that there was no change in the total level of GluA1 expression in cells upon CCNY overexpression (FIG. 5F). These results show that CCNY regulates the expression of the AMPA receptor on the cell surface.

13. Result #3

Figure 6A:
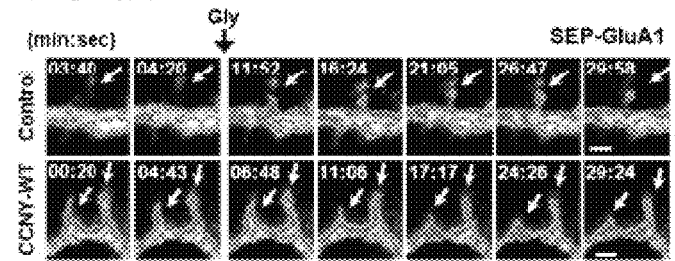
FIG. 6 shows that CCNY inhibits GluA1 delivery to the cell surface in a long-term potentiation (LTP) model, which is known as a cellular mechanism for memory. When CCNY is overexpressed, glycine-induced GluA1 exocytosis, which is a cellular readout of LTP expression, is decreased (FIGS. 6A and 6C). When CCNY expression is decreased by shRNA, the glycine-induced GluA1 exocytosis is increased (FIGS. 6B and 6C). Such an increase is recovered when shRNA-resistant CCNY is simultaneously overexpressed (FIGS. 6B and 6C).
Figure 6B:
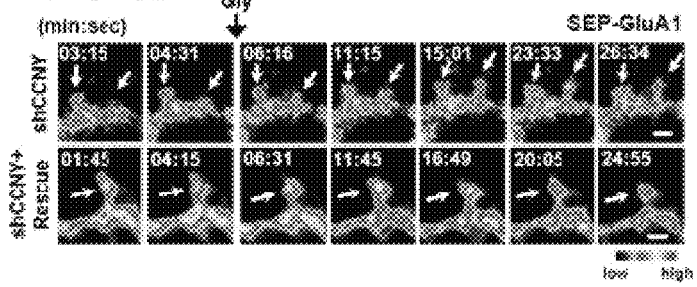
Figure 6C:
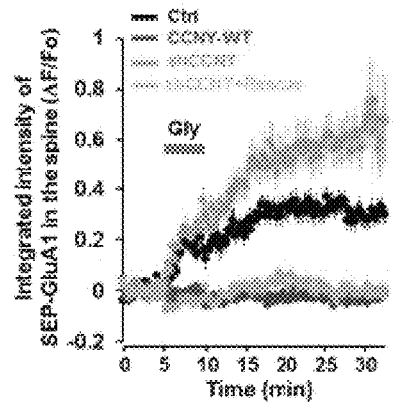
Figure 7A:
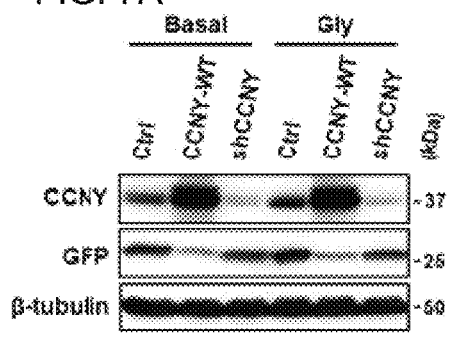
FIG. 7 shows that there is no alteration in the expression level of CCNY protein in the LTP model (FIGS. 7A and 7B). After infecting hippocampal neurons with lentivirus expressing CCNY shRNA or CCNY-WT, the expression level of CCNY was detected by immunoblot analysis before and after the glycine treatment which is an LTP-inducing memory improvement protocol.
Figure 7B:
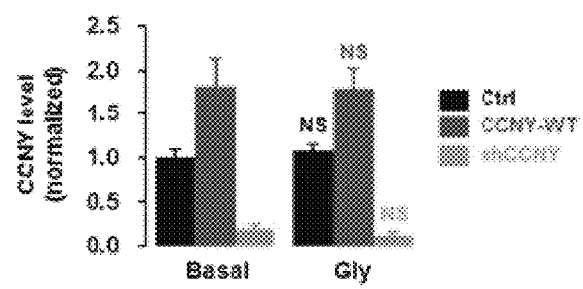
Figure 8A:
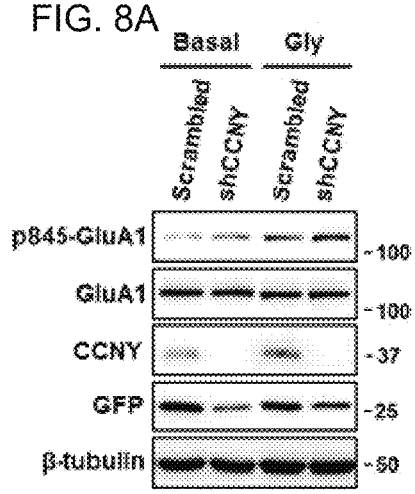
FIG. 8 shows that the phosphorylation of GluA1 S845 which is known to be increased in the LTP model is further increased when CCNY function is inhibited (FIGS. 8A and 8B). After infecting hippocampal neurons with lentivirus expressing CCNY shRNA, the phosphorylated level of GluA1 at the site of S845 was detected by immunoblot analysis before and after the glycine treatment which is an experiment regarding memory improvement.
Figure 8B:
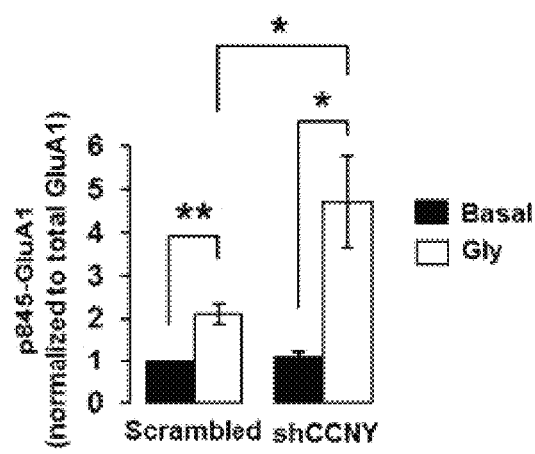

One of the forms of synaptic plasticity that has been most widely studied in the mammalian central nervous system is long-term potentiation (LTP). LTP refers to a long-lasting increase in synaptic strength that is achieved by an increase in the number of AMPA receptors in synapses via the AMPA receptor exocytosis. LTP is believed to be a cellular mechanism for learning and memory (Malenka and Nicoll, 1999; Malinow et al., 2000). In particular, there have been previous studies showing that AMPA receptors containing GluA1 subunits are important for LTP expression (Passafaro et al., 2001; Shi et al., 2001). Therefore, it was then investigated whether CCNY regulates the delivery of GluA1 to the cell surface in an LTP model, which is known as a cellular mechanism of memory. To selectively visualize surface GluA1, superecliptic pHuorin (SEP)-GluA1 was used. To induce LTP, primary cultured hippocampal neurons were treated with 200 μM glycine (3 minutes; temperature ranging from room temperature to 32° C.). A decrease in glycine-induced GluA1 exocytosis was observed upon CCNY overexpression (FIGS. 6A and 6C). In contrast, an increase in the glycine-induced GluA1 exocytosis was observed upon CCNY knockdown by shRNA (FIGS. 6B and 6C). Such an increase was rescued when shRNA-resistant CCNY was simultaneously overexpressed (FIGS. 6B and 6C). In this LTP model, the CCNY protein expression level was not altered (FIGS. 7A and 7B). In addition, the phosphorylation of GluA1 S845, which is known to be increased in the LTP model, was observed to be further increased when the CCNY function was inhibited by shRNA (FIGS. 8A and 8B). These results show that CCNY functions to negatively regulate LTP, which is known as a cellular mechanism of memory.

4. Result #4

Figure 9C:
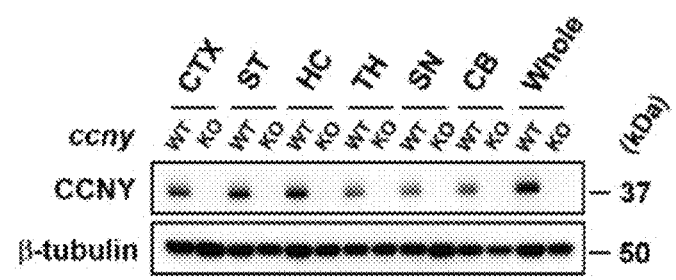

Given that CCNY regulates functional LTP by inhibiting synaptic delivery of AMPARs in the hippocampus, it is hypothesized that CCNY plays an important role in cognition of learning and memory. To test this, we first generated ccny KO mice using the CRISPR/Cas9 system. The ccny KO mice we generated have a 31-bp deletion, spanning the first exon and the first intron of ccny gene (FIG. 9A), and this was confirmed by PCR genotyping (FIG. 9B). The ccny KO mice completely lacked CCNY protein in the sub-regions of the brain (FIG. 9C).

5. Result #5

We next tested whether CCNY regulates hippocampal-dependent spatial memory by performing the Morris water maze task with ccny KO mice. Latency to platform was significantly shorter on Days 4 and 5 in ccny KO mice than in wild type mice during the training sessions (FIGS. 10A and 10B), indicating an enhancement of learning ability in ccny KO mice. In addition, latency to platform zone, where the platform was originally located, was significantly reduced (FIG. 10C), and time spent in the target quadrant was also reasonably increased in ccny KO mice during the probe test on Day 6 (FIG. 10D), indicating an enhancement of memory ability in ccny KO mice.

A spatial reversal learning task was then applied by placing the hidden platform in a new location, the opposite quadrant from the previously memorized quadrant. In ccny KO mice, latency to platform was significantly shorter on Day 3 during the reversal learning training sessions (FIG. 10E), and latency to platform zone was also significantly reduced on Day 4 of the reversal learning probe test (FIG. 10F), indicating that memory flexibility (new learning and memory) is also significantly better in ccny KO mice than wild type mice.

A visible test with the ccny KO mice, showing no significant differences both in the latency to platform during the training sessions (FIG. 10G) and in the latency to platform zone during the probe test (FIG. 10H), supports that such enhanced learning abilities in the original Morris water maze task (FIGS. 10A-10D) and the reversal learning task (FIGS. 10E and 10F) were not due to the change of locomotive ability in ccny KO mice. Taken together, our data show that lack of CCNY protein in ccny KO mice improves spatial learning ability, indicating an inhibitory role of CCNY in the learning and memory cognitive brain function.

In the present invention, it was observed that decreased expression level of CCNY protein elicited synaptic delivery of GluA1, and ccny KO mice showed an enhanced learning and memory function. In contrast, it was also observed that increased expression level of CCNY protein inhibited synaptic delivery of GluA1, which may impair learning and memory (FIG. 11). Therefore, it is highly plausible that a composition inhibiting CCNY function contributes to the improvement of learning and memory.

EFFECT OF THE INVENTION

The present invention may reveal a CCNY-oriented molecular mechanism with respect to learning and memory, help understand causes of brain diseases associated with memory problems, and ultimately be applied in the treatment and diagnosis of brain memory disorders such as dementia.

What is claimed is:

1. A method for increasing long-term potentiation (LTP) in a subject comprising: administering to the subject a composition for increasing long-term potentiation (LTP), which comprises a Cyclin Y (CCNY) inhibitor as an active ingredient; wherein the CCNY inhibitor is an antisense oligonucleotide complementary to the entire coding region or complementary to a portion of the coding region of a nucleic acid molecule encoding CCNY; and wherein the antisense oligonucleotide inhibits the activity of the CCNY protein.

* * * * *